(12) United States Patent
Uvacek

(10) Patent No.: US 10,754,016 B1
(45) Date of Patent: Aug. 25, 2020

(54) SYSTEMS AND METHODS FOR ULTRASOUND PHASE ADJUSTMENT

(71) Applicant: White Eagle Sonic Technologies, Inc., Santa Clara, CA (US)

(72) Inventor: Bohumir Uvacek, Hayward, CA (US)

(73) Assignee: White Eagle Sonic Technologies, Inc., Santa Clara, CA (US)

(*) Notice: Subject to any disclaimer, the term of this patent is extended or adjusted under 35 U.S.C. 154(b) by 353 days.

(21) Appl. No.: 15/912,366

(22) Filed: Mar. 5, 2018

Related U.S. Application Data

(60) Provisional application No. 62/466,888, filed on Mar. 3, 2017.

(51) Int. Cl.
| | | |
|---|---|---|
| *G01S 7/52* | (2006.01) | |
| *G10K 11/34* | (2006.01) | |
| *A61B 8/08* | (2006.01) | |
| *A61B 8/00* | (2006.01) | |

(52) U.S. Cl.
CPC ........ *G01S 7/52046* (2013.01); *A61B 8/5207* (2013.01); *G10K 11/346* (2013.01); *A61B 8/585* (2013.01)

(58) Field of Classification Search
CPC . G01S 7/52046; G10K 11/346; A61B 8/5207; A61B 8/585
See application file for complete search history.

(56) References Cited

U.S. PATENT DOCUMENTS

| | | | |
|---|---|---|---|
| 4,501,002 A | * | 2/1985 | Auchterlonie ...... H04L 27/2273 329/309 |
| 5,856,955 A | | 1/1999 | Cole et al. |
| 5,891,038 A | | 4/1999 | Seyed-Bolorforosh et al. |
| 5,913,823 A | | 6/1999 | Hedberg et al. |
| 6,104,673 A | | 8/2000 | Cole et al. |
| 6,172,939 B1 | | 1/2001 | Cole et al. |
| 6,277,073 B1 | | 8/2001 | Bolorforosh et al. |

(Continued)

FOREIGN PATENT DOCUMENTS

| | | |
|---|---|---|
| CN | 101403727 | 4/2009 |
| WO | WO-2011/135472 | 11/2011 |
| WO | WO-2012/049591 | 4/2012 |

*Primary Examiner* — Daniel Pihulic
(74) *Attorney, Agent, or Firm* — Womble Bond Dickinson (US) LLP

(57) ABSTRACT

The system adjusts the phase of an ultrasound channel by removing sample clock voltage pulses from a rectangular electrical waveform that drives the transducer. Each channel's transducer applies or acts as a band-pass filter in the conversion of the electrical waveform to mechanical motion, generating an ultrasound sine wave. Removing clock voltage pulses from the electrical waveform can shift the phase of the ultrasound by an amount less than a sample clock period. The system focuses and directs the ultrasound during shooting at a specific angle by applying phase delays to successive channels. Removing sample clock voltage pulses allows the system to shoot at smaller angles and create a greater scan density and focal point density of imaging data and reduces the power. Partial sample clock voltage pulses may also be removed. If needed, the system can increase the power by adjusting the power supply voltages. The system can utilize a lower frequency clock generator lowering the power utilization.

30 Claims, 5 Drawing Sheets

(56) References Cited

U.S. PATENT DOCUMENTS

| | | |
|---|---|---|
| 6,363,033 B1 | 3/2002 | Cole et al. |
| 6,461,299 B1 | 10/2002 | Hossack |
| 6,551,244 B1 | 4/2003 | Gee |
| 6,905,467 B2 | 6/2005 | Bradley et al. |
| 6,971,992 B2 | 12/2005 | Cerofolini |
| 7,780,597 B2 | 8/2010 | Panda et al. |
| 8,147,409 B2 | 4/2012 | Shifrin |
| 8,668,647 B2 | 3/2014 | Eskandari et al. |
| 8,712,716 B2 | 4/2014 | Thomas et al. |
| 8,717,210 B2 | 5/2014 | Eldar et al. |
| 8,836,557 B2 | 9/2014 | Eldar et al. |
| 8,958,408 B1 | 2/2015 | Jain et al. |
| 9,060,669 B1 | 6/2015 | Mo et al. |
| 9,132,287 B2 | 9/2015 | Mast et al. |
| 2001/0051771 A1 | 12/2001 | Bradley et al. |
| 2004/0077945 A1 | 4/2004 | Cerofolini |
| 2006/0173342 A1 | 8/2006 | Panda et al. |
| 2008/0242987 A1 | 10/2008 | Shifrin |
| 2010/0312150 A1 | 12/2010 | Mast et al. |
| 2012/0095323 A1 | 4/2012 | Eskandari et al. |
| 2013/0030726 A1 | 1/2013 | Thomas et al. |
| 2013/0038479 A1 | 2/2013 | Eldar et al. |
| 2013/0187682 A1 | 7/2013 | Eldar et al. |
| 2013/0324187 A1* | 12/2013 | Master .................. H04W 48/12 455/552.1 |
| 2014/0323871 A1 | 10/2014 | Bardelli et al. |

\* cited by examiner

SYSTEMS AND METHODS FOR ULTRASOUND PHASE ADJUSTMENT

CROSS-REFERENCE TO RELATED APPLICATIONS

This application claims the benefit of U.S. Provisional Patent Application No. 62/466,888 filed Mar. 3, 2017, the entirety of which is incorporated herein by reference.

BACKGROUND OF THE INVENTION

1. Field of the Invention

This invention relates to the field of ultrasound imaging and in particular to ultrasound imaging systems which steer or focus ultrasound waves during shooting. More particularly the invention relates to a system, and method for steering ultrasound waves by generating a phase delay between transducers.

2. Prior Art

Ultrasound imaging systems control probe units causing them to generate and receive ultrasound acoustic waves. Probe units typically have hundreds of transducers which are capable of shooting separate acoustic waves and receiving acoustic waves. In many ultrasound applications it is advantageous to control the acoustic wave shooting by introducing a time delay between the shooting at different transducers. This has the effect of steering the acoustic waves and can be used to create a parallel beam in a required direction or to create a focused beam that converges at a required focal point. The shooting time delay between transducers is often referred to as a phase delay or phase shift in their respective waveforms.

U.S. Pat. Nos. 6,104,673; 8,147,409; and 9,132,287 discuss systems and methods for steering ultrasound waves. These systems employ special-purpose hardware making the ultrasound system more expensive and have limits on the minimum phase delay.

Ultrasound systems would benefit if there was a way to reduce the minimum phase delay. This would allow greater beam density and better image resolution in applications such as those with a high focal depth or with tiny steps in steering angles like in ultrafast imaging. Many ultrasound users want the benefits of a reduced minimum phase delay in a low-power, portable ultrasound system.

DETAILED DESCRIPTION OF THE PREFERRED EMBODIMENTS

Figure 1:
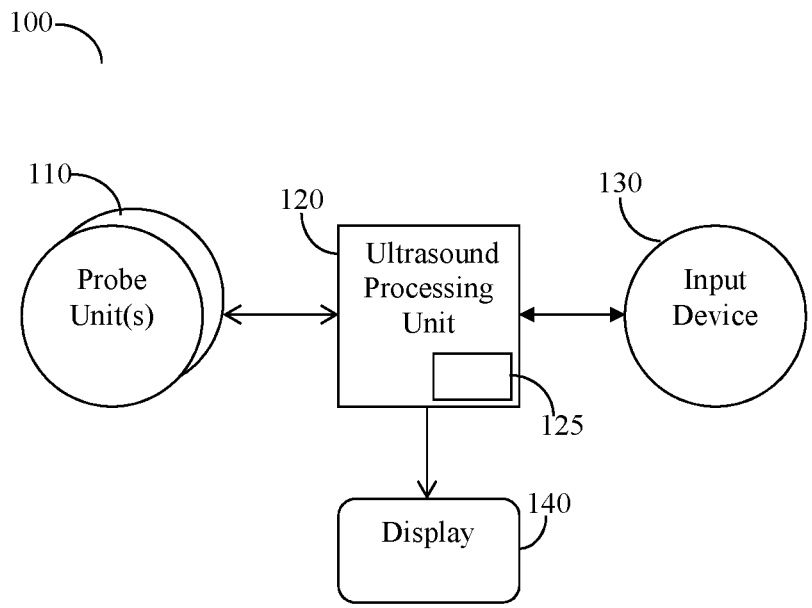
FIG. 1 shows an exemplary ultrasound system.

FIG. 1 is an exemplary diagram of an ultrasound system. The ultrasound system 100 is coupled to one or more probe units 110. Each probe unit 110 typically controls one or more transducers embodied therein. The transducers are typically elements capable of transmitting and receiving ultrasound beams. Some specialized probe units 110 have separate transducers for transmission and reception of ultrasound. Probe units 110 have transducers arranged in many geometrical shapes including a linear array, a curved linear array, a radial array or 2-D array. The ultrasound system 100 further comprises an ultrasound processing unit 120 to control the probe units 110. The ultrasound processing unit 120 sends probe control commands, telling the probe units 110 which probe is selected and defines when to fire specific beams and when to collect data. Such operation, as explained in further detail herein below, is performed, for example, from a memory 125 containing instructions that are executed by the ultrasound processing unit 120. The ultrasound processing unit 120 is configured to further process data collected by a probe unit 110. The ultrasound processing unit 120 takes input commands from one or more input devices 130.

The input devices 130 typically provide high-level commands to the ultrasound processing unit 120 which in turn, under control of the embedded instruction memory 125 performs at least the tasks described in greater detail herein below. The ultrasound processing unit 120 outputs at least a result respective of the data collected to, for example, a display unit 140. A display unit 140 may be replaced or augmented by a storage unit (not shown) to allow the storing of the collected data for future use. The display unit 140 may show an image, a video comprised of a series of image frames, text, and the like, as well as combinations thereof.

Figure 2:
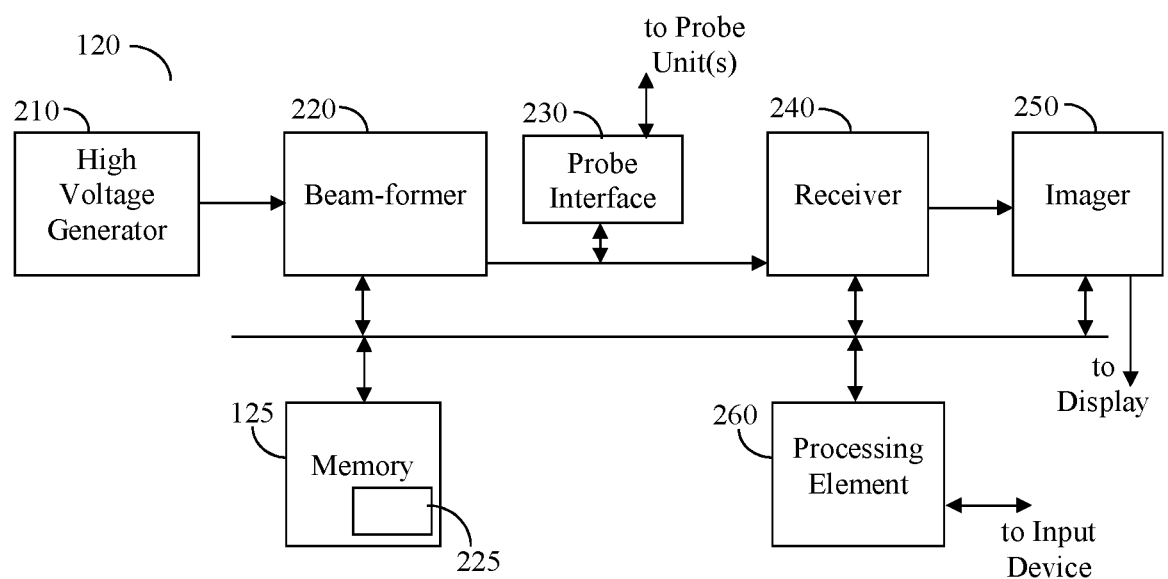
FIG. 2 shows a detailed diagram of the processing unit of the ultrasound system according to an embodiment.

FIG. 2 is an exemplary and non-limiting detailed diagram of the ultrasound processing unit 120 of the ultrasound system 100 according to an embodiment. The ultrasound processing unit 120 comprises a high voltage generator 210 that is coupled to a beam-former 220. The high voltage generator 210 provides the high voltage necessary for the proper operations of at least the probes 110 coupled to the processing unit 120 through probe interface 230 which is coupled to the beam-former 220. The probe interface 230 is further coupled to a receiver 240 that is configured to receive and shape signals from the probe providing them to an imager 250 coupled to the receiver 240. The imager 250 is configured to couple to a display 140. The beam-former 220, receiver 240 and imager 250 are coupled to a processing element 260 that is further coupled to a memory 125. In one embodiment the ultrasound processing unit 120 contains multiple processing elements 260 coupled to multiple memories 125. The memory 125 contains instructions that when executed by the processor element 260 cause the ultrasound processing unit 120 to operate according to the principles of the invention, and as further described herein in greater detail. The memory 125 may be further used to save at least images generated by the imager 250. The memory 125 also holds digital waveform representations 225. The digital waveform representations 225 define the format of the electrical waveforms to be generated by the beam-former 220 and sent to the probes 110. Processing unit 120 generates the digital waveform representations 225 based on inputs from device 130. One of ordinary skill in the art would readily appreciate that the memory 125 may be further used for saving and retrieving other data without departing from the scope of the invention. It should be appreciated that in one embodiment the ultrasound processing unit 120 may be implemented as a monolithic integrated circuit (IC) which may or may not include certain elements thereof. For example, high voltage circuitry may be implemented off-chip. Furthermore, the ultrasound processing unit 120 may be implemented in whole or in part on a monolithic IC, including but not limited to a system on chip (SoC) implementation.

Figure 3:
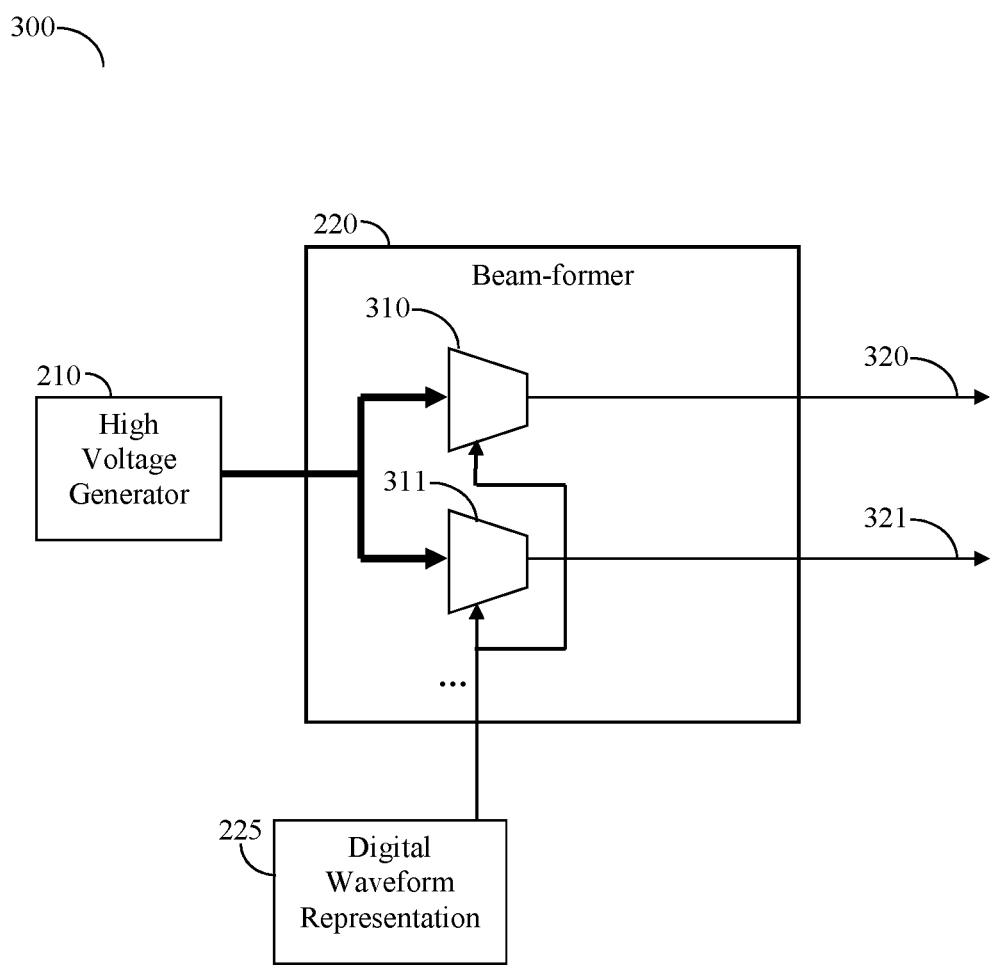
FIG. 3 shows a diagram of the electrical waveform generator of the beam-former according to an embodiment.

FIG. 3 is an exemplary and non-limiting diagram 300 showing the electrical wave generation of the beam-former 220 according to an embodiment. The high voltage generator 210 provides multiple voltage levels to the beam-former 220. In one embodiment the high voltage generator 210 provides multiple configurable voltage levels of up to +100, +50, 0, −50, and −100 volts. Most probes have an electrical power requirement that requires a voltage lower than 100V. The electrical power depends on the amplitude (i.e., voltage) and frequency of the electrical waveform. The ultrasound system 100 sets the voltage levels to match the requirements of the probes 110. The beam-former 220 has multiple multiplexers, such as 310 and 311, that select one of the voltage levels to generate electrical waveforms such as 320 and 321. The beam-former 220 generates independent waveforms that drive each transducer of the probes 110. In one embodiment the beam-former 220 is capable of generating 4096 independent waveforms driving 4096 transducers at the same time. The beam-former 220 selects a voltage level for each clock cycle of a sampling clock. In one embodiment the sampling clock runs at 40 MHz. The probes 110 typically operate at 1-10 MHz but in extreme cases 10 KHz to 25 MHz. The beam-former 220 drives a 10 MHz probe transducer by creating a rectangular wave of 10 MHz. In this example, the beam-former 220 selects a high voltage level for 4 sample clock pulses and then selects a low or zero voltage level for 4 sample clock pulse periods. The transducer applies or acts as a band-pass filter in the conversion of the electrical waveform to mechanical motion, to produce an acoustic sinusoidal waveform. The beam-former 220 reads the digital waveform representations 225 from memory 125. The digital waveform representations 225 define the voltage level for each sample clock pulse.

Figure 4A:
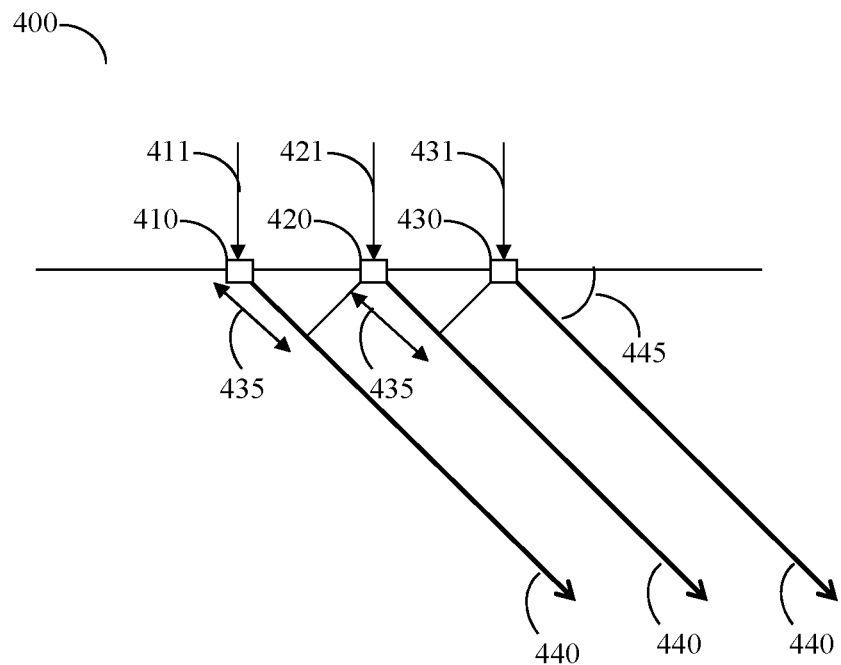
FIGS. 4a and 4b show diagrams that illustrate beam steering and focusing.

FIG. 4a is a diagram 400 that illustrates beam steering. Electrical waveforms 411, 421 and 431 drive transducers 410, 420 and 430 respectively. Transducers 410, 420 and 430 generate acoustic waves 440. If electrical waveforms 431 and 421 are delayed relative to their neighboring waveform by time 435, the acoustic beam 430 will act as a parallel beam at shooting angle 445. The relative delay is called a phase delay. The direction of the parallel acoustic beam depends on the phase delay. Having a large range of possible phase delays allows to the system to shoot in many possible directions.

Figure 4B:
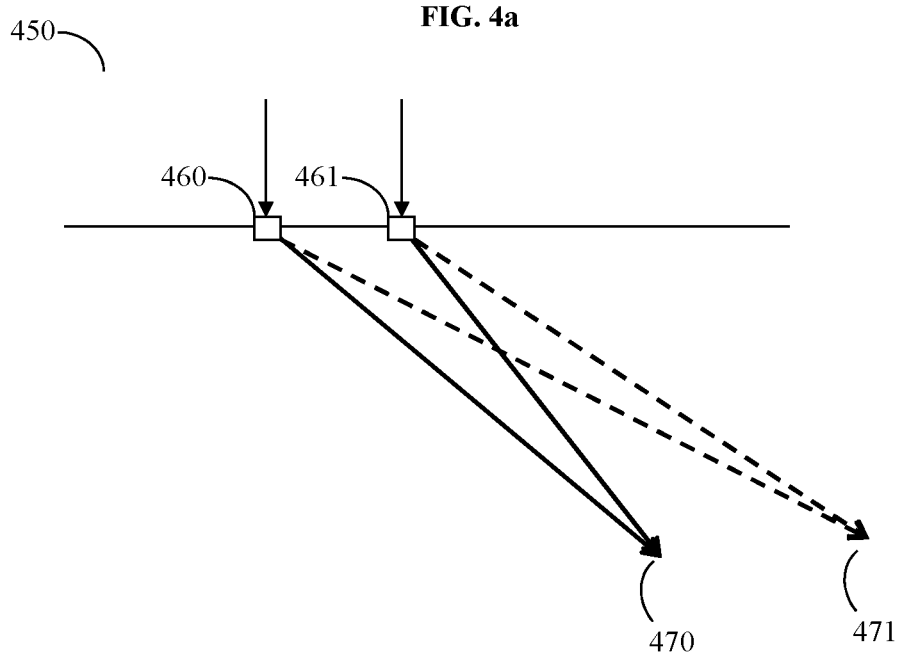

FIG. 4b is a diagram 450 that illustrates beam focusing. At one point in time transducers 460 and 461 are focused at point 470. At a later point in time transducers 460 and 461 are focused at point 471. To focus waves from all transducers on one focal point the excitation pulses are delayed such that their travel time from each transducer to the focal point is the same. If the focal points 470 and 471 are far away, for example more than 1 meter, the ultrasound system will need to use small phase delays to generate a clear image. Smaller phase delays are required to increase the density of focal points.

Figure 5A:
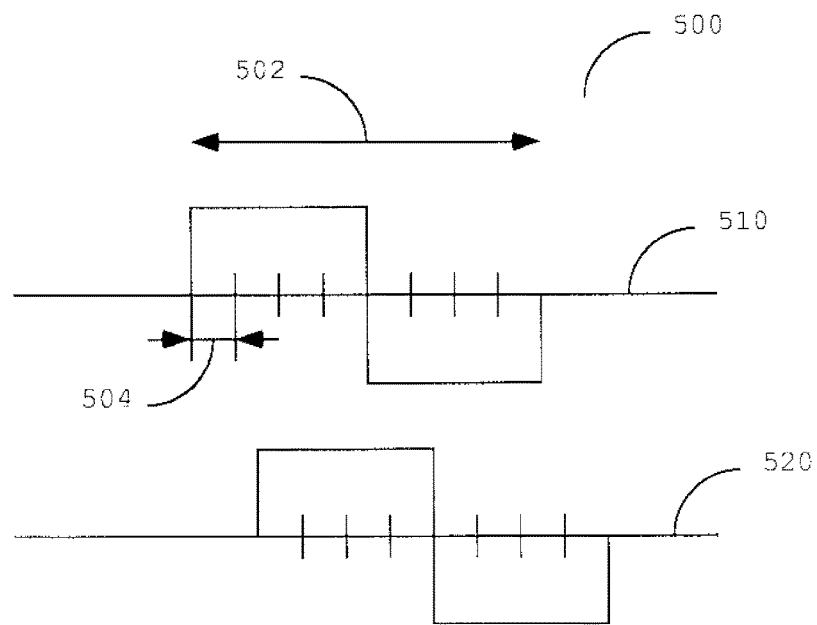
FIG. 5a shows exemplary electrical waveforms for beam steering and focusing that differ by a full sample clock pulses.

FIG. 5a is a diagram 500 that shows exemplary electrical waveforms created by the ultrasound processing unit 120. Waveforms 510 and 520 are derived from the same sample clock which has clock period 504. Waveforms 510 and 520 drive two transducers to generate acoustic waves with the same frequency and different phase. Waveform 510 has a clock period 502 made up of 8 sample clock periods 504. Waveform 520 is shifted by one sample clock period 504 relative to waveform 510. In this example the beam-former 220 steers a beam by introducing a phase delay of one sample clock period 504. Waveform 510 is described using digital waveform representation 225 as "22220000" where each "2" represents high positive voltage and each "0" represents a high negative voltage. The digital waveform representation 225 defines the voltage level for each sample clock period. Similarly, waveform 520 is described using digital waveform representation 225 as "122220000" where the "1" represents the ground level of voltage.

Figure 5B:
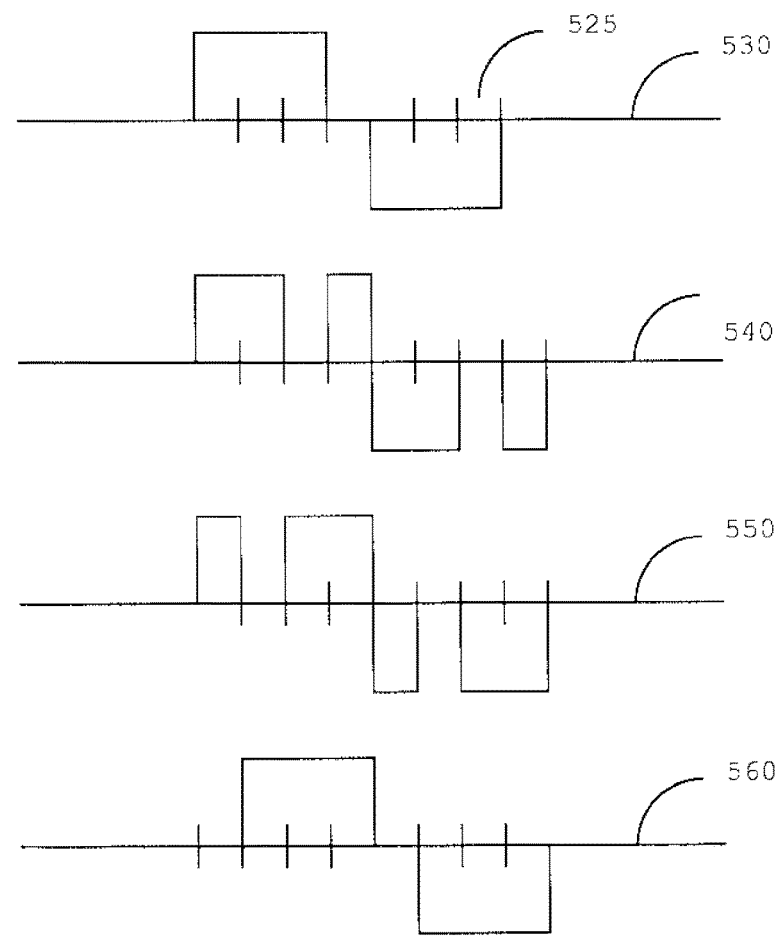
FIG. 5b shows exemplary electrical waveforms for beam steering and focusing that have removed sample clock voltage pulses.

FIG. 5b is a diagram 525 that shows exemplary electrical waveforms with removed sample clock voltage pulses created by the ultrasound processing unit 120. The beam-former 220 steers beams using phase delays smaller than a full sample clock period 504 by effectively removing rectangular chunks of the waveform. We call this phase shift a sub-sample clock pulse period phase shift. Waveforms 530, 540, 550 and 560 are examples of waveforms that produce sub-sample clock pulse period phase shifts. Waveform 530 is described using digital waveform representation 225 as "22210001" and is derived from waveform 510 by making the waveform zero at sample clock times 4 and 8. The transducer will apply or act as a band-pass filter to the electrical waveform and create a sinusoidal acoustic wave that has a sub-sample clock pulse period phase shift to the left. Similarly waveform 540 is derived from waveform 510 by making the waveform zero at sample clock times 3 and 6 and waveform 550 is derived from waveform 510 by making the waveform zero at sample clock times 2 and 5. Waveform 560 is shifted by one sample clock period 504 relative to waveform 530. Waveforms 530, 540, 550 and 560 produce a sub-sample clock pulse period phase shift of one third of a sample clock period 504 relative to each other. More such waveforms are created to match the number of transducers. Utilizing waveforms 530 and 560 produces the same single sample phase shift (but not the same phase) as utilizing waveforms 510 and 520, respectively.

In a system with a 160 MHz sampling clock driving a 1 MHz probe and using 5 possible voltage levels (V1, V2, 0, −V2, −V1), the beam-former can produce a large number of possible waveforms that offer a large choice of sub-sample clock pulse period phase shifts. In this example, the basic waveform will consist of 80 clock cycles of high voltage and 80 cycles of low voltage. Having the above 5 possible voltage levels allows the beam-former to effectively remove one or more sample clock voltage pulses of V1 or V2, or effectively remove one or more sample clock voltage pulses of V1 and effectively remove one or more sample clock voltage pulses of V2. Selecting an intermediate voltage V2 of one half of V1 allows the removal of a half sample clock voltage pulse. With 5 possible voltage levels the digital waveform representation consists of digits from 0-4. In practice the electrical components of the beam-former may not be able to switch voltage levels quickly enough to produce a true rectangular waveform. In this case the actual phase shift is less than that predicted by assuming instantaneous transitions. To ameliorate this issue the beam-former selects waveforms with two or more adjacent sample clock pulses removed.

The exact phase delay depends on the speed of the electronics. For high precision beam forming the beam-former should be calibrated to measure actual phase delays with selected probes.

Diagram 525 illustrates a simple example with only 3 voltage levels (V, 0, −V) and 8 sample clock periods per waveform period. Removing a sample clock voltage pulse of the waveform reduces the power of the waveform. Waveforms 530, 540, 550 and 560 each have the same power which is three quarters of the power of waveforms 510 and 520. The beam-former normally uses waveforms with the same power and adjusts the voltage levels of the power supply to match the probe requirements for those waveforms. For example, after first shooting with waveforms 530, 540, 550 and 560 to get a sub-sample clock pulse period phase shift or delay; the beam-former may later shoot using waveforms 530 and 560 to get a full sample clock period phase delay. In this case the beam-former uses the waveforms 530 and 560 instead of waveforms 510 and 520 because waveforms 530 and 560 have the same power as waveforms 540 and 550. Adjusting the voltage levels of the power supply takes time and the shooting time interval is normally smaller than the time required for adjusting the voltage. The beam-former typically adjusts the voltage slowly over several frames of image data based on user controls.

Referring again to FIG. 5b, it will be noted that waveforms 530 and 560 are the same, with waveform 560 merely starting one sample clock pulse period later. Since there are two intervening phase shifts between waveforms 530 and 560 in this example, it would be expected that the intervening phase shifts are one third and two thirds of a sample clock pulse period with respect to sample clock pulse waveform 530.

An ultrasound system with a 160 MHz sample clock frequency typically uses a 40 MHz crystal connected to a phase-lock loop that multiplies the sampling clock frequency. This 160 MHz ultrasound system uses more than four times the power of a 40 MHz ultrasound system using the 40 MHz crystal. A 40 MHz ultrasound system using the sample clock voltage pulse removal technique can in some cases approximate the behavior of the 160 MHz ultrasound system while using less than one quarter of the overall power. In a preferred embodiment the ultrasound system can operate at multiple, selectable frequencies offering a range of power utilization.

Figure 6:
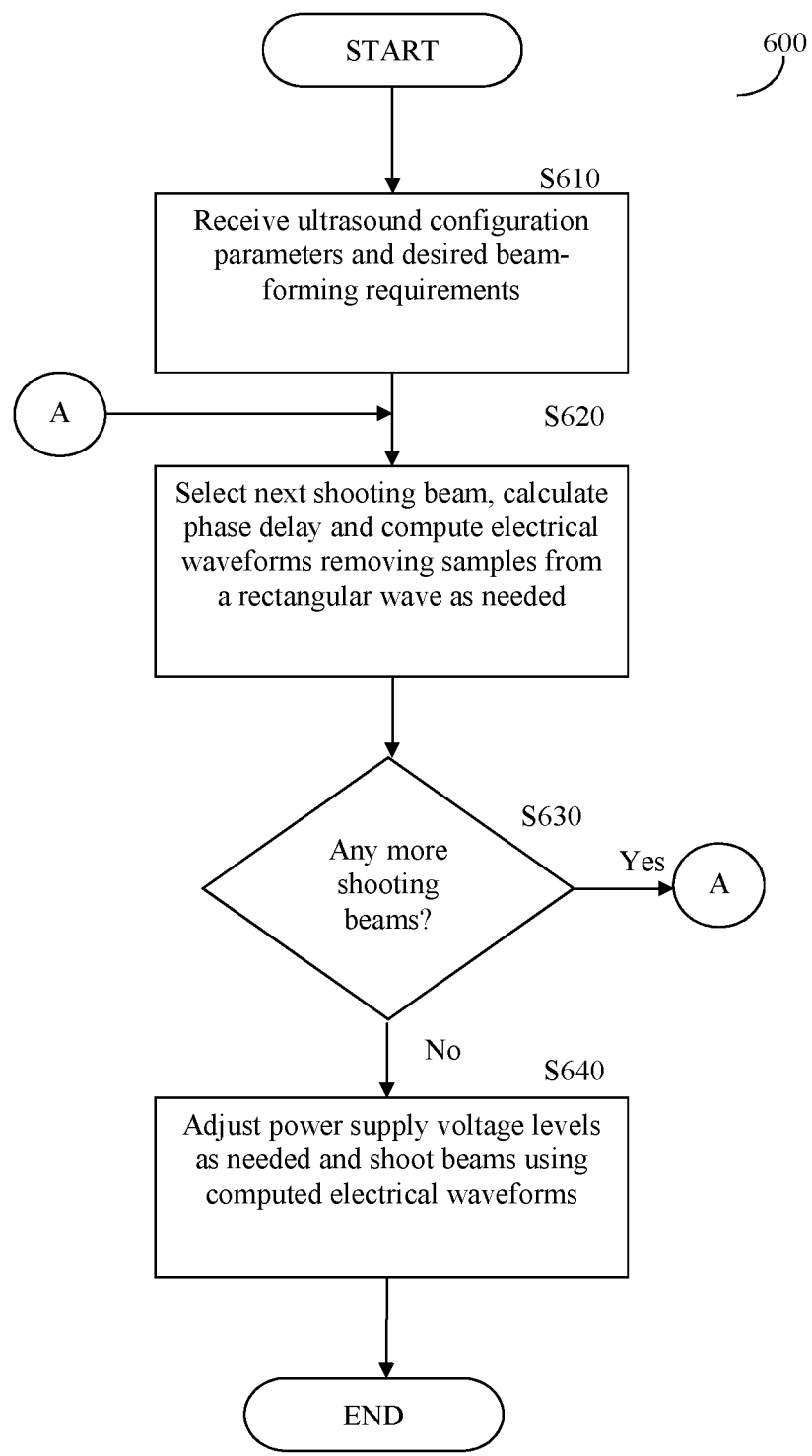
FIG. 6 shows a flowchart of the operation of the ultrasound processing unit according to an embodiment.

FIG. 6 shows a flowchart 600 of the operation of the ultrasound processing unit according to an embodiment. In S610 the processing unit receives a description of the current ultrasound system configuration and the desired beam-forming requirements. The current ultrasound system configuration includes power supply parameters of number of possible voltage levels; probe parameters of number of transducers, possible shooting frequencies, probe geometry and required probe power; and ultrasound system parameters of sample clock frequencies. The desired beam-forming requirements can be expressed in multiple ways. The desired beam-forming requirements typically include ultrasound type (e.g., B-Mode imaging), number of beams, number of parallel beams, transmit frequency, number of cycles, starting depth, ending depth, focal depth, transmit frequency stop, receive frequency stop, receive window, beam angle and center angle. The desired beam-forming requirements are specified by an end-user typically interacting with an application program. The end-user may specify high-level requirements and allow the application program to supply detailed requirements.

In S620 the ultrasound processing unit selects the next shooting beam and processes it. Step S620 is the start of loop that processes all shooting beams, one by one. The number of shooting beams may be given directly as part of the beam-forming requirements or may be implied from other parameters. The shooting angle for the current shooting beam is computed from the number of beams, center angle, beam angle and similar parameters. The shooting angle defines the required phase delay. For large phase delays, those larger than the sample clock frequency period, the ultrasound processing unit selects a whole number of sample clock pulse periods plus the transducer drive waveform and drive voltage(s) that will produce the desired sub-sample clock pulse period phase shift, to adjust the phase. The ultrasound processing unit defines a starting rectangular waveform with period corresponding to the transmit frequency and then defines phase-shifted rectangular waveforms, with one waveform per transducer. For sub-sample clock pulse period phase shifts, those smaller than the sample clock period, the ultrasound processing unit determines how many sample clock voltage pulses to remove from the rectangular waveform. In a preferred embodiment, the ultrasound processing unit removes the same number of sample clock voltage pulses (and partial pulses if used) from the positive and negative segments of the waveform in the same half waveform positions to maintain the same frequency of each sample clock voltage pulse and same power in all transducer drive waveforms in a frame. The ultrasound processing unit computes the waveforms and stores the computed waveforms in the digital waveform representation in memory. In a preferred embodiment the ultrasound system removes the same number of sample clock voltage pulses from each waveform used to produce a frame of image data. This ensures that the waveforms have the same power.

In S630 the ultrasound processing unit determines if it has processed all the shooting beams. If the ultrasound processing unit has finished processing all the shooting beams it continues at S640. If the ultrasound processing unit has not finished processing all the shooting beams it continues at S620. In S640 the ultrasound processing unit adjusts if necessary the power supply voltages to match the probe requirements for the current set of electrical waveforms. The ultrasound processing unit directs the beam-former to shoot the beams by reading the digital waveform representation in memory and using it to generate electrical waveforms.

In the embodiments hereinbefore described, at least one sample clock voltage pulse is omitted in each half of the voltage waveform applied to the respective transducer of the probe. In systems that simply use a single transducer drive voltage and zero volts, the transducer drive waveform period would still be a plurality of sample clock periods, but would not necessarily be an even multiple of the sample clock periods, and the one (or more) sample clock voltage pulses may be removed from the part of the voltage waveform applied to the respective transducer, the position of which will provide the control of the sub-sample clock period phase shift.

In systems having 5 possible voltage levels (V1, V2, 0, −V2, −V1) or more, one could remove (or add) not only one (or more) sample clock voltage pulses preferably from each of the positive and negative waveform portions as hereinbefore described, but also one or more partial sample clock voltages pulses by using the smaller voltage of V1 and V2 in place of the larger voltage of V1 and V2 for the respective sample clock time period (or vice versa). Other variations include removing sample clock voltage pulses or sample clock voltage pulses and partial sample clock voltage pulses that are not adjacent each other in the transducer drive waveform or half waveform. These and other variations may be used to achieve sub-sample clock period phase shifts of the present invention as desired or appropriate for the specific ultrasound processing unit being used.

In the described embodiments the ultrasound processing unit computes all waveforms for all shootings before it starts shooting. In second embodiments the ultrasound processing unit computes waveforms in real-time during shooting.

The embodiments disclosed herein can be implemented as hardware, or at least in part in firmware or software, or any combination thereof. Moreover, a software portion is preferably implemented as an application program tangibly embodied on a program storage unit or computer readable medium. The application program may be uploaded to, and executed by a machine of any suitable architecture. Preferably, that machine is implemented on a computer platform having hardware such as one or more central processing units ("CPUs"), one or more memories, and one or more input/output interfaces. The computer platform may also include an operating system and microinstruction code. The various processes and functions described herein may be either part of the microinstruction code or part of the application program, or any combination thereof, which may be executed by a CPU, whether or not such computer or processor is explicitly shown. In addition, various other peripheral units may be connected to the computer platform such as an additional data storage unit and a printing unit.

Thus the present invention has a number of aspects, which aspects may be practiced alone or in various combinations or sub-combinations, as desired. While a preferred embodiment of the present invention has been disclosed and described herein for purposes of illustration and not for purposes of limitation, it will be understood by those skilled in the art that various changes in form and detail may be made therein without departing from the spirit and scope of the invention as defined by the full breadth of the following claims.

What is claimed is:

1. A method of ultrasound imaging system phase adjustment comprising:
   providing an ultrasound processing unit for use with a probe unit having a plurality of transducers responsive to transducer drive voltage waveforms and having a predetermined transmit frequency with a transmit frequency period;
   providing sample clock pulses, each sample clock pulse having a sample clock pulse period, each period of the predetermined transmit frequency being equal to a first plurality of sample clock pulse periods;
   the first plurality of sample clock periods being equal to a second plurality of sample clock periods during which sample clock voltage pulses of a first polarity can be coupled to a respective transducer plus a third plurality of sample clock periods during which sample clock voltage pulses of the first polarity will not be coupled to a respective transducer;
   forming transducer drive voltage waveforms, each for driving a respective transducer in a probe unit, each transducer drive voltage waveform being formed by a first series of sample clock voltage pulses of the first polarity in the second plurality of sample clock periods, the first series of sample clock voltage pulses of the first polarity being less in number than the second plurality of sample clock periods so that each transducer drive voltage waveform is missing at least one sample clock voltage pulse of the first polarity, the position of the missing sample clock voltage pulse of the first polarity within each first series of sample clock pulses determining a phase shift between transducer drive voltage waveforms for driving transducers in a probe unit which phase shifts include sub-sample clock period phase shifts between transducer drive voltage waveforms for driving transducers in a probe unit, whereby sub-sample clock pulse period phase shifts may be created in the transducer drive voltage waveforms for driving transducers in a probe unit.

2. The method of claim 1 wherein the transducer drive voltage waveforms are zero volts during sample clock periods when sample clock voltage pulses of the first polarity will not be coupled to the respective transducer, including sample clock periods during which a transducer drive voltage waveform is missing at least one sample clock voltage pulse of the first polarity.

3. The method of claim 1 further comprising providing a probe unit having the plurality of transducers responsive to the transducer drive voltage waveforms and having the predetermined transmit frequency having the transmit frequency period, and applying each transducer drive voltage waveform to a respective transducer in the probe unit.

4. The method of claim 1 wherein no sample clock voltage pulses are applied to the transducers during the third plurality of sample clock periods.

5. The method of claim 1 wherein the first series of sample clock voltage pulses is less in number than the second plurality of sample clock periods by at least two so that each transducer drive voltage waveform is missing at least two sample clock voltage pulses in the respective transducer drive voltage waveform, the position of the missing sample clock voltage pulses within each series of sample clock pulses of the transducer drive voltage waveforms determining the phase shift between transducer drive voltage waveforms.

6. The method of claim 5 wherein the missing sample clock voltage pulses are during adjacent clock pulse periods.

7. The method of claim 1 wherein forming transducer drive voltage waveforms includes forming at least one additional sample clock voltage pulse of a voltage different from the sample clock voltage pulses of claim 1 and including the additional sample clock voltage pulse in the series of sample clock voltage pulses in the second plurality of sample clock periods, the positions of the missing sample clock voltage pulse and the one additional sample clock voltage pulse of a voltage different from the sample clock voltage pulses of claim 1 within each first series of sample clock pulses of each transducer drive voltage waveform determining a phase shift between transducer drive voltage waveforms.

8. The method of claim 1 wherein the first plurality of sample clock periods is an even plurality of sample clock periods and wherein the second plurality of sample clock periods is equal in number to the third plurality of sample clock periods, and wherein during the third plurality of sample clock periods, sample clock voltage pulses of a second plurality polarity may be coupled to the respective transducer.

9. The method of claim 8 wherein forming transducer drive voltage waveforms further comprises forming transducer drive voltage waveforms having a series of sample clock voltage pulses of a second polarity in the third plurality of sample clock periods equal in number to the number of sample clock voltage pulses in the second plurality of sample clock periods, whereby the series of sample clock voltage pulses of the second polarity is less in number than the third plurality of sample clock periods so that each transducer drive voltage waveform is also missing at least one sample clock voltage pulse of the second polarity in the respective transducer drive voltage waveform, the position of the missing sample clock voltage pulse of the second polarity within each series of sample clock pulses of the second polarity also determining a sub-sample clock period phase shifts between transducer drive voltage waveforms.

10. The method of claim 1 wherein the transducer drive voltage waveforms are zero volts during sample clock periods when a transducer drive voltage waveform is missing any sample clock voltage pulse of either polarity.

11. The method of claim 9 wherein the pattern of the number of missing sample clock voltage pulses of the second polarity is the same as the pattern of missing sample clock voltage pulses of the first polarity.

12. The method of claim 11 wherein the magnitude of the voltage of each sample clock pulse voltage of the second polarity is the same as the magnitude of the voltage of the corresponding sample clock pulse voltage of the first polarity.

13. The method of claim 12 wherein the first series of sample clock voltage pulses is less in number than the second plurality of sample clock periods by at least two so that each transducer drive voltage waveform is missing at least two sample clock voltage pulses of each plurality in the respective transducer drive voltage waveform, the position of the missing sample clock voltage pulses within each series of sample clock pulses determining a phase shift between transducer drive voltage waveforms.

14. The method of claim 13 wherein the missing sample clock voltage pulses of each polarity are during adjacent clock pulse periods for sample clock voltage pulses of the respective polarity.

15. The method of claim 11 wherein forming transducer drive voltage waveforms further comprises forming at least one additional sample clock voltage pulse of the first polarity and of a voltage different from the sample clock voltage pulses of the first polarity of claim 9, forming at least one additional sample clock voltage pulse of the second polarity and of a magnitude equal to the at least one additional sample clock voltage pulse of the first polarity, and including the additional sample clock voltage pulse in the respective first and second series of sample clock voltage pulse.

16. An ultrasound imaging system comprising:
an ultrasound processing unit for coupling to a probe unit having a first plurality of transducers and having a predetermined transmit frequency with an associated transmit frequency period, the ultrasound imaging system having a processor element, a memory and a beam former;
an input device coupled to the ultrasound processing unit for providing input commands to the ultrasound processing unit;
the ultrasound processing unit for providing sample clock pulses, each sample clock pulse having a sample clock pulse period, each period of the predetermined transmit frequency being equal to a first plurality of sample clock pulse periods, the first plurality of sample clock periods being equal to a second plurality of sample clock periods during which sample clock voltage pulses of a first polarity can be coupled to a respective transducer plus a third plurality of sample clock periods during which sample clock voltage pulses of the first polarity are not coupled to the respective transducer;

the beam former forming transducer drive voltage waveforms, each for driving a respective transducer in a probe unit, each transducer drive voltage waveform being formed by a first series of sample clock voltage pulses of the first polarity in the second plurality of sample clock periods, the first series of sample clock voltage pulses of the first polarity being less in number than the second plurality of sample clock periods so that each transducer drive voltage waveform is missing at least one sample clock voltage pulse of the first polarity, the position of the missing sample clock voltage pulse of the first polarity within each first series of sample clock pulses determining a phase shift between transducer drive voltage waveforms for driving transducers in a probe unit which phase shifts include sub-sample clock period phase shifts between transducer drive voltage waveforms for driving transducers in a probe unit, whereby sub-sample clock pulse period phase shifts may be created in the transducer drive voltage waveforms for driving transducers in a probe unit.

17. The system of claim 16 further comprising providing a probe unit having the plurality of transducers responsive to the transducer drive voltage waveforms and having the predetermined transmit frequency having the transmit frequency period, each transducer drive voltage waveform being coupled to a respective transducer in the probe unit.

18. The system of claim 16 wherein the beam former forms transducer drive voltage waveforms missing at least two neighboring sample clock pulses.

19. The system of claim 16 further comprising a power supply for providing a plurality of voltages, the beam former being coupled to the power supply to receive a voltage to associate with each sample clock pulse forming each electrical waveform for driving each transducer.

20. The system of claim 16 wherein the beam former forms transducer drive voltage waveforms with no sample clock voltage pulses during the third plurality of sample clock periods.

21. The system of claim 16 wherein the beam former forms transducer drive voltage waveforms wherein the first series of sample clock voltage pulses is less in number than the second plurality of sample clock periods by at least two so that each transducer drive voltage waveform is missing at least two sample clock voltage pulses in the respective transducer drive voltage waveform, the position of the missing sample clock voltage pulses within each series of sample clock pulses of the transducer drive voltage waveforms determining the phase shift between transducer drive voltage waveforms.

22. The system of claim 21 wherein the beam former forms transducer drive voltage waveforms wherein at least some of the missing sample clock voltage pulses are during adjacent clock pulse periods.

23. The system of claim 16 wherein the beam former forms transducer drive voltage waveforms having at least one additional sample clock voltage pulse of a voltage different from the sample clock voltage pulses of claim 14 and including the additional sample clock voltage pulse in the series of sample clock voltage pulses in the second plurality of sample clock periods, the positions of the missing sample clock voltage pulse and the one additional sample clock voltage pulse of a voltage different from the sample clock voltage pulses of claim 14 within each first series of sample clock pulses of each transducer drive voltage waveform determining a phase shift between transducer drive voltage waveforms.

24. The system of claim 16 wherein the beam former forms transducer drive voltage waveforms wherein the first plurality of sample clock periods is an even plurality of sample clock periods and wherein the second plurality of sample clock periods is equal in number to the third plurality of sample clock periods, and wherein during the third plurality of sample clock periods, sample clock voltage pulses of a second plurality polarity may be coupled to the respective transducer.

25. The system of claim 24 wherein the beam former forms transducer drive voltage waveforms having a series of sample clock voltage pulses of a second polarity in the third plurality of sample clock periods equal in number to the number of sample clock voltage pulses in the second plurality of sample clock periods, whereby the series of sample clock voltage pulses of the second polarity is less in number than the third plurality of sample clock periods so that each transducer drive voltage waveform is also missing at least one sample clock voltage pulse of the second polarity in the respective transducer drive voltage waveform, the position of the missing sample clock voltage pulse of the second polarity within each series of sample clock pulses of the second polarity also determining a sub-sample clock period phase shifts between transducer drive voltage waveforms.

26. The system of claim 25 wherein the beam former forms transducer drive voltage waveforms wherein the pattern of the number of missing sample clock voltage pulses of the second polarity is the same as the pattern of missing sample clock voltage pulses of the first polarity.

27. The system of claim 26 wherein the beam former forms transducer drive voltage waveforms wherein the magnitude of the voltage of each sample clock pulse voltage of the second polarity is the same as the magnitude of the voltage of the corresponding sample clock pulse voltage of the first polarity.

28. The system of claim 27 wherein the beam former forms transducer drive voltage waveforms wherein the first series of sample clock voltage pulses is less in number than the second plurality of sample clock periods by at least two so that each transducer drive voltage waveform is missing at least two sample clock voltage pulses of each plurality in the respective transducer drive voltage waveform, the position of the missing sample clock voltage pulses within each series of sample clock pulses determining a phase shift between transducer drive voltage waveforms.

29. The system of claim 28 wherein the beam former forms transducer drive voltage waveforms wherein the missing sample clock voltage pulses of each polarity are during adjacent clock pulse periods for sample clock voltage pulses of the respective polarity.

30. The system of claim 29 wherein the beam former further forms at least one additional sample clock voltage pulse of the first polarity and of a voltage different from the sample clock voltage pulses of the first polarity of claim 27, forming at least one additional sample clock voltage pulse of the second polarity and of a magnitude equal to the at least one additional sample clock voltage pulse of the first polarity, and including the additional sample clock voltage pulse in the respective first and second series of sample clock voltage pulses.

* * * * *